US010321822B1

(12) United States Patent
Lee et al.

(10) Patent No.: US 10,321,822 B1
(45) Date of Patent: Jun. 18, 2019

(54) NON-MYDRIATIC SELF-IMAGING FUNDUS CAMERA

(71) Applicant: Verily Life Sciences LLC, Mountain View, CA (US)

(72) Inventors: Seung Ah Lee, San Francisco, CA (US); Chinmay George Belthangady, San Francisco, CA (US); Charles M. Santori, Palo Alto, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 0 days.

(21) Appl. No.: 15/728,087

(22) Filed: Oct. 9, 2017

Related U.S. Application Data

(60) Provisional application No. 62/409,528, filed on Oct. 18, 2016.

(51) Int. Cl.
A61B 3/14 (2006.01)
A61B 3/10 (2006.01)
A61B 3/02 (2006.01)
A61B 3/00 (2006.01)
A61B 3/15 (2006.01)
A61B 3/12 (2006.01)

(52) U.S. Cl.
CPC .............. A61B 3/152 (2013.01); A61B 3/12 (2013.01)

(58) Field of Classification Search
CPC ........... A61B 3/152; A61B 3/103; A61B 3/14; A61B 3/113; A61B 3/1225; A61B 3/024; A61B 3/18; A61B 3/1015
USPC ....... 351/208, 200, 205, 206, 209, 210, 221, 351/222, 245, 246
See application file for complete search history.

(56) References Cited

U.S. PATENT DOCUMENTS

| 6,733,129 | B2 | 5/2004 | Masaki |
| 7,458,685 | B2 | 12/2008 | Liang et al. |
| 7,499,634 | B2 | 3/2009 | Yogesan et al. |
| 7,878,653 | B2 | 2/2011 | Ichikawa et al. |
| 7,954,949 | B2 | 6/2011 | Suzuki |
| 9,125,559 | B2 | 9/2015 | Kersting et al. |

(Continued)

OTHER PUBLICATIONS

TRC-NW8 Non-Mydriatic Retinal Camera, Retrieved from internet: http://www.topconmedical.com/products/trcnw8.htm on Aug. 31, 2016, 2 pages.

(Continued)

Primary Examiner — Dawayne Pinkney
(74) Attorney, Agent, or Firm — Christensen O'Connor Johnson Kindness PLLC

(57) ABSTRACT

A fundus camera and method of operating the fundus camera are described. The fundus camera includes an image sensor, an eyepiece lens, an illumination source, and an alignment target. The image sensor captures image light of a retina within an eye. The eyepiece lens is disposed to pass the image light of the retina to the image sensor. The illumination source is disposed to direct illumination light onto the retina through the eyepiece lens. The illumination source is further disposed around a first aperture through which the image light of the retina passes from the eyepiece lens to the image sensor. The alignment target is coupled to output an alignment image through the eyepiece lens to the eye and disposed around a second aperture through which the image light of the retina is passed to the image sensor and the illumination light is passed to the eyepiece lens.

25 Claims, 8 Drawing Sheets

(56) References Cited

U.S. PATENT DOCUMENTS

| | | | | |
|---|---|---|---|---|
| 2003/0208125 A1* | 11/2003 | Watkins | ............... | A61B 3/12 600/473 |
| 2007/0236661 A1* | 10/2007 | Fukuma | ............... | A61B 3/102 351/205 |
| 2009/0069794 A1* | 3/2009 | Kurtz | ............... | A61F 9/00825 606/4 |
| 2012/0218518 A1* | 8/2012 | Wada | ............... | A61B 3/1005 351/208 |
| 2013/0208243 A1 | 8/2013 | Sakagawa | | |
| 2014/0313485 A1* | 10/2014 | Umekawa | ............... | A61B 3/103 351/211 |
| 2016/0174838 A1 | 6/2016 | Herranen et al. | | |

OTHER PUBLICATIONS

Volk Optical—Volk Pictor Plus Portable Retinal Camera #RCV9001-000, Retrieved from internet: http://www.veatchinstruments.com/Volk-Pictor-Plus-Portable-Retinal-C on Aug. 31, 2016, 3 pages.

CenterVue International Web Site, Retrieved form Internet: https://www.centervue.com/ on Aug. 31, 2016, 5 pages.

eyeSelfie: Self Directed Eye Alignment using Reciprocal Eye Box Imaging, Retrieved from internet: http://web.media.mit.edu/~tswedish/projects/eyeSelfie.html on Aug. 31, 2016, 3 pages.

Matos, Luciana de et al., "Coaxial fundus camera for ophthalmology", Retrieved from internet: http://spiedigitallibrary.org/ on Jun. 23, 2016, Proc. of SPIE vol. 9578 957813-1, 5 pages.

Hastings, Art Jr., "Eye Box Performance Parameters for Non Pupil Forming Head/Helmet Mounted Displays", PPT 521, Dec. 6, 2006, 6 pages.

DeHoog, E. et al., "Optimal parameters for retinal illumination and imaging in fundus cameras", Applied Optics, vol. 47, No. 36, Dec. 20, 2008, 9 pages.

* cited by examiner

NON-MYDRIATIC SELF-IMAGING FUNDUS CAMERA

CROSS-REFERENCE TO RELATED APPLICATION

This application claims the benefit of U.S. Provisional Application No. 62/409,528, filed Oct. 18, 2016, which is incorporated by reference in its entirety.

TECHNICAL FIELD

This disclosure relates generally to imaging technologies, and in particular, relates to fundus cameras.

BACKGROUND INFORMATION

Fundus imaging is a part of basic eye exams, yet the size, cost and complexity of conventional retinal cameras limit the availability of fundus imaging for screening, field diagnosis, and progress monitoring of many retinal diseases. Wide-field fundus imaging is difficult due to the low reflectivity of the fundus, the small eye pupil size, and the high background noise from corneal and iris reflections. Most commercial wide-field fundus cameras employ complex optical designs to image the fundus while avoiding corneal and iris reflections, which require precise lateral and axial alignment of the camera to the patient's pupil.

In both table-top and portable realizations of conventional fundus cameras, fundus imaging usually requires either pupil dilation using dilation agents or a trained operator aided with infra-red imaging for the alignment. There are automated systems that utilize closed-loop optomechanical feedback for camera alignment, but still suffer from large system size and cost, as well as, a slow alignment process.

Recently, a self-imaging portable retinal camera has been developed using a separate fixation path with a set of pinhole masks placed near and on the conjugate plane to the retina that confine the ray angles. However, this design suffers from a small imaging field-of-view compared to state-of-the-art commercial systems and the self-alignment scheme is based on pupil-forming pinhole masks, which result in a low imaging yield.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
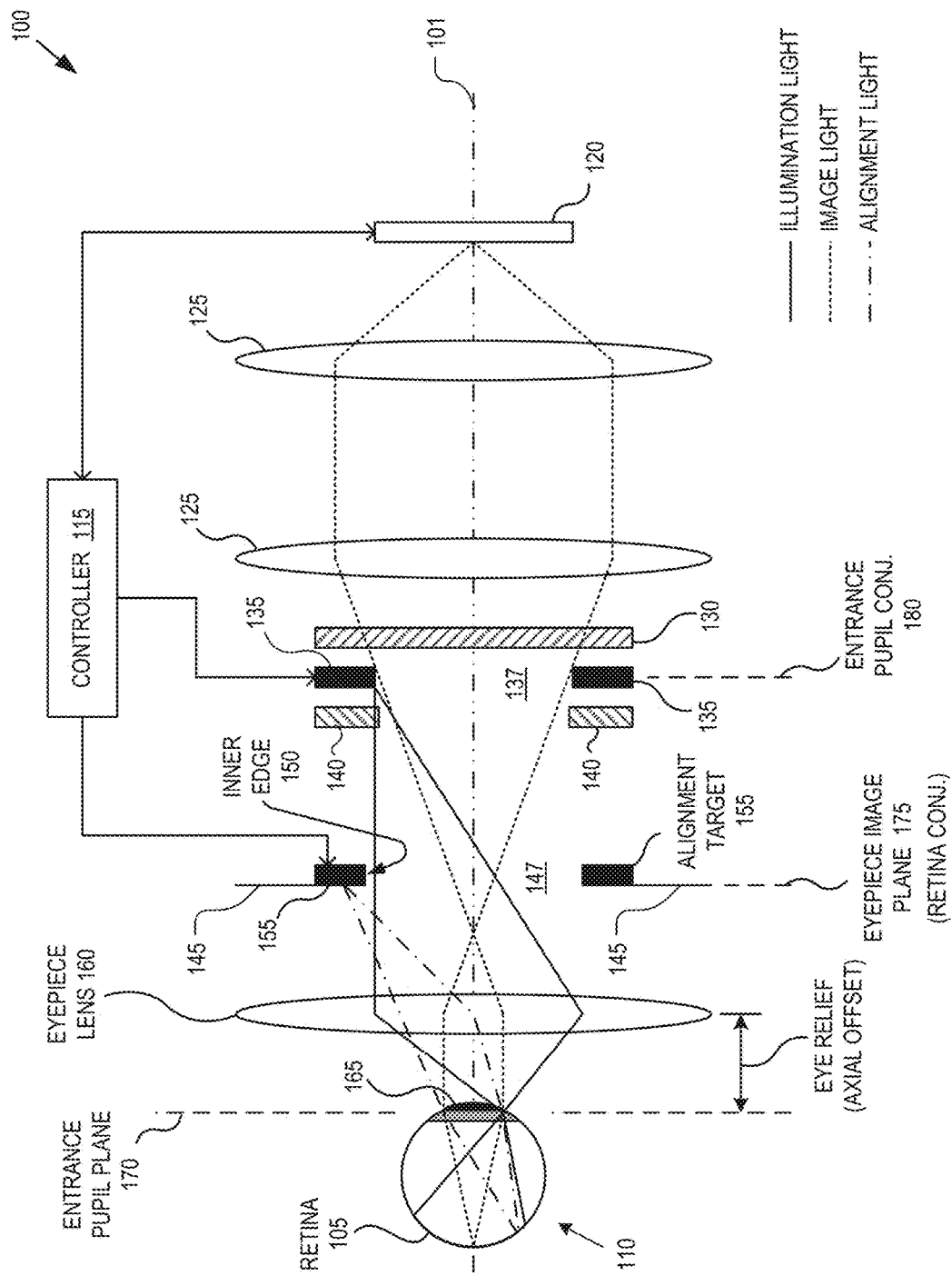
FIG. 1 is an illustration of a fundus camera system for self-imaging of a retina, in accordance with an embodiment of the disclosure.

Embodiments of a system, apparatus, and method of use of a fundus camera system capable of enabling wide-field, self-imaging of a user's retina are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Conventional fundus cameras require an eye care professional for alignment. A self-aligning fundus camera is a fundus camera where a patient can take fundus images by him or herself. Such self-aligning fundus cameras provide some sort of feedback to the patient through an optical path different from the image path from the eye through the eyepiece to the image sensor. Such self-aligning fundus cameras also generally have eye tracking mechanisms to calculate the feedback given to the patient.

In various embodiments described herein, a self aligning fundus camera provides an alignment target (which may be different from a fixation target) comprised of at least two illuminated concentric shapes on an image plane between the eyepiece and the image sensor. The concentric shapes can be centered around the image path but outside the field of view of the image sensor so as not to interfere with fundus imaging.

An alignment target is used to provide feedback to the patient such that the patient can place his/her head and eye within the intended "eye-box" (i.e., "the volume of space within which an effectively viewable image is formed by a lens system or visual display, representing a combination of exit pupil size and eye relief distance"). In contrast, a fixation target is used to help the patient eye's focus reach a defined distance (e.g., infinity). In some cases, the brightness and/or contrast of the fixation target can be higher than that of the alignment target such that the alignment target in the peripheral vision of the patient's field-of-view does not distract the patient from looking at the fixation target.

For axial movement alignment, the patient can be instructed to adjust his/her position (while maintaining focus on the fixation target) until at least one of the concentric shapes in his/her peripheral vision is visible and at least one of the concentric shapes is not visible. For lateral movement alignment, the patient can also be instructed to adjust his/her position until the visible concentric shape's border is visible. In one example, the illuminated concentric shapes are circles. In one example, the illuminated concentric shapes are displayed by a microdisplay, a ring of light emitting diodes, or any other light source, light deflectors, optical guide, or otherwise.

When utilizing the concentric shapes as an alignment target, the accuracy of the alignment may be affected by the pupil size of the patient's eye. Accordingly, in some embodiments, the image sensor can detect the pupil size and adjust the size of the concentric shapes based on the pupil size. In some embodiments, the alignment target includes multiple concentric shapes, and the patient can self-select which of the concentric shapes to use for alignment. In some embodiments, the fundus camera can shine light on the patient's eye in order to decrease pupil size prior to alignment.

Embodiments disclosed herein describe a wide-field, non-mydriatic fundus camera that enables self-imaging of the fundus or retina. The fundus is the rear interior surface of the eye that includes the retina, optic disc, macula, fovea, and posterior pole. The design enables a compact and low-cost realization of a fundus camera that guides the user to self-align their eye to the camera and thus can remove the need for a trained camera operator for precise alignment. Embodiments of this self-imaging fundus camera can be useful for screening, early diagnosis, and long-term monitoring of various retinal diseases. In some embodiments, the fundus camera system may be packaged as a portable handheld camera that the user holds up to their eye (monocular implementations) or eyes (binocular implementations). In other embodiments, the fundus camera system may be packaged as a tabletop system, a desktop system, or a wall mounted system that incorporates chin and forehead rests for added stability.

FIG. 1 is an illustration of a fundus camera system 100 for self-imaging of a retina 105 of an eye 110, in accordance with an embodiment of the disclosure. Fundus camera system 100 illustrates a single optical path for implementing a monocular fundus camera; however, it should be appreciated that the components along the optical path may be replicated for two eyes in binocular implementations. The illustrated embodiment of fundus camera system 100 includes a controller 115, an image sensor 120, one or more focusing lenses 125 (two are illustrated), a polarization plate 130, an illumination ring 135, a polarizing ring 140, a field stop 145 having an inner edge 150, an alignment target 155, and an eyepiece lens 160. In the illustrated embodiment, eye 110 includes a pupil 165, which resides along an entrance pupil plane 170 as perceived by fundus camera system 100. When fundus camera system 100 is correctly aligned to eye 110 and focused for imaging retina 105, field stop 145 and an emissive aperture of alignment target 155 are positioned along an eyepiece image plane 175 (which is also a conjugate plane to retina 105) while illumination ring 135 is positioned along a conjugate plane 180 to entrance pupil plane 170 (also referred to as an entrance pupil conjugate).

Retinal cameras can include three optical paths: an illumination path, an imaging path, and an eye fixation path. In conventional retinal cameras, the three paths are often combined using beam splitters or holed mirrors to project the fixation path into the user's field of view (FOV). In contrast, the illustrated embodiments of fundus camera system 100 combines the illumination path of illumination light with the imaging path of image light and an alignment path of alignment light by concentrically aligning alignment target 155, illumination ring 135, and image sensor 120 about a common center optical axis 101. While in some embodiments image sensor 120 may be repositioned off center optical axis 101 using various optical elements, by aligning all three components (alignment target 155, illumination ring 135, and image sensor 120) about center optical axis 101, a compact form factor is achieved that reduces the overall number of optical components (e.g., mirrors, beam splitters, lenses, etc.).

Alignment target 155 outputs an alignment image that serves as a visual cue in the user's/patient's peripheral vision to perform a self-alignment between fundus camera system 100 and their eye within a small margin of error required for wide-field fundus imaging with reduced background noise from corneal and iris reflections. In some embodiments, alignment target 155 further operates as an accommodation target in the user's peripheral vision for aiding eye accommodation to infinity.

During operation, controller 115 controls and orchestrates the operation and timing of the other electronic components of fundus camera system 100. In particular, controller 115 can activate/deactivate alignment target 155 for eye alignment. Additionally, controller 115 can synchronize the flashing of illumination ring 135 with a shutter signal to image sensor 120 to acquire an image of retina 105 at the time of illumination. In one embodiment, controller 115 is a microcontroller executing software/firmware instructions. In another embodiment, controller 115 is an application specific integrated circuitry (ASIC), field programmable gate array (FPGA), or other hardware logic. Controller 115 may further include memory for storing retinal images output from image sensor 120. Image sensor 120 may be implemented using a variety of technologies including a charged coupled device (CCD) image sensor, a complementary metal-oxide-semiconductor (CMOS) image sensor, or otherwise.

Illumination ring 135 is a ring shaped (e.g., circular, elliptical, square, hexagonal, etc.) light emitter with an aperture 137 disposed in its center to pass the image light received through eyepiece lens 160 to image sensor 120. A ring shaped illuminator provides high contrast retinal images by rejecting corneal reflections through angular separation. In one embodiment, illumination ring 135 is a circular array of light emitting diodes (LEDs) mounted along an annular shaped substrate. In another embodiment, illumination ring 135 is a series of optic fibers having emission apertures embedded around an annular shaped substrate and input apertures coupled to one or more light sources. In an alternative embodiment, illumination ring 135 is a ring-shaped reflector that is illuminated by an off-axis lamp source. The light sources may emit visible wavelengths and/or near-infrared wavelengths. For example, infrared emitters may be interspersed with visible light emitters to aid in autofocusing. In the illustrated embodiment, illumination ring 135 is axially aligned about center optical axis 101 and resides on conjugate plane 180 to entrance pupil plane 170 when fundus camera system 100 is aligned. However, it should be appreciated that illumination ring 135 need not exactly reside on conjugate plane 180, but rather may reside adjacent to conjugate plane 180 within tolerances permitted by alignment eyebox 505 (see FIG. 505C).

The diffuse reflections from retina 105 are collected through pupil 165 and aperture 137 in illumination ring 135 by image sensor 120. In one embodiment, aperture 137 through illumination ring 135 is the limiting aperture for image sensor 120 and fundus camera 100. Image sensor 120 is positioned on a conjugate plane to eyepiece image plane 175. In the illustrated embodiment, the back reflections of the illumination light off of eyepiece lens 160 are rejected using a cross-polarization scheme. For example, ring polarizer 140 is positioned in front of illumination ring 135 to polarize the output illumination light along a first polarization axis and polarizing plate 130 is placed behind aperture 137 to polarize the reflected light along a second polarization axis orthogonal to the first polarization axis, thereby passing only cross-polarized diffuse reflectance from retina 105. In one embodiment, the ring polarizer 140 and plate polarizer 130 are linear polarizers with orthogonal orientations. To further reduce deleterious back reflections, the surfaces of eyepiece lens 160 may be coated with anti-reflection (AR) films.

Figure 2:
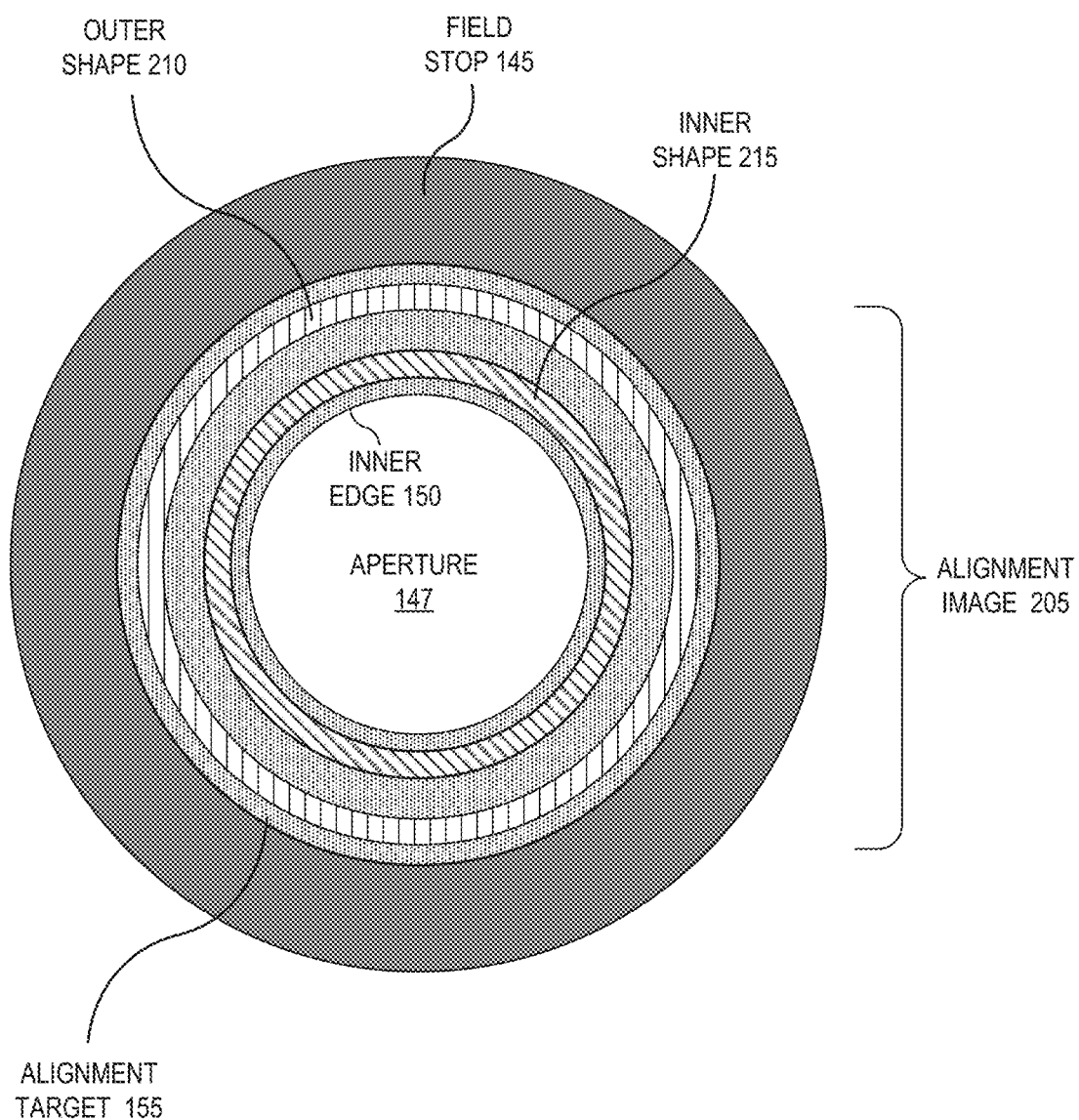
FIG. 2 is an illustration of an alignment target and field stop of the fundus camera system, in accordance with an embodiment of the disclosure.

FIG. 2 is an illustration of alignment target 155 and field stop 145, in accordance with an embodiment of the disclosure. The illustrated embodiment of alignment target 155 outputs an alignment image 205 that includes an outer shape 210 and an inner shape 215 concentrically aligned around aperture 147. The inner edge 150 of field stop 145 and/or alignment target 155 define aperture 147. In some embodiments, the opaque portions of alignment target 155 external to outer shape 210 and inner shape 215 operate as the field stop 145. Alignment target 155 and field stop 145 are positioned between eyepiece lens 160 and illumination ring 135 along a common plane. As illustrated in FIG. 1, the common plane is eyepiece image plane 175, which is also a conjugate plane to retina 105 when eye 110 is aligned to fundus camera system 100.

Alignment target 155 may be implemented as an alignment target display using a variety of technologies, such as, an array of LED lights, one or two annulus shaped light guides each with a backlight, an light emitter with a center hole and blackout regions to define the outer shape 205 and inner shape 215, or other display technologies. In another embodiment, alignment target 155 is formed from two concentric arrays of optic fibers having emission apertures mounted in concentric annular shapes to a substrate and input apertures positioned to collect the alignment light from one or more light sources. In one embodiment, alignment image 205 is monochromatic. In another embodiment, alignment image 205 is multi-color with inner shape 215 having a first color (e.g., green) or first pattern (e.g., dots, dashes, etc.) that is different from a second color (e.g., red) or second pattern of outer shape 210. The differing colors or patterns can be helpful to the user to differentiate inner shape 215 from outer shape 210, since these shapes are positioned in their peripheral vision. Although FIG. 2 illustrates outer shape 210 and inner shape 215 as being concentric, solid, circles, other shapes or patterns may be used. In fact, a number of patterns (e.g., colors, dots, dashes, etc.) and shapes (e.g., square, etc.) that are concentric about center optical axis 101 may be used. In additional to color, shape, and pattern variations, temporal variations may also be used to distinguish the inner and outer shapes. For example, temporal variations such as blinking, variable brightness/color, and shape moving (e.g., rotating) may be used.

Returning to FIG. 2, alignment image 205, including outer shape 210 and inner shape 215, serves as a visual cue to the user for self-alignment of fundus camera system 100 to eye 110 and in particular to pupil 165 (discussed in detail in connection with FIGS. 4 and 5A-5D). Alignment image 205 is emitted towards eye 110 from a location that is peripheral of inner edge 150 of field stop 145. As such, alignment image 205 is outside the FOV of image sensor 120 and seen by the user in their peripheral vision when fundus camera system 100 is aligned. Alignment target 155 is designed such that the proper alignment image 205 is seen by the user when eye 110 is aligned within an eyebox region (e.g., see alignment eyebox 505 in FIG. 5C) that ensures acceptable retinal imaging quality. The size (or diameter) of inner edge 150 may be selected to be equal to or larger than the size of the image of retina 105 (for a selected field of view) formed at eyepiece image plane 175. In one embodiment, axial offset alignment is achieved when the user can see inner shape 215 (i.e., inner shape 215 is within the user's FOV), but cannot see outer shape 210 (i.e., outer shape 210 is outside the user's FOV). In one embodiment, lateral alignment is achieved by centering alignment target 155 in the user's FOV.

Figure 3:
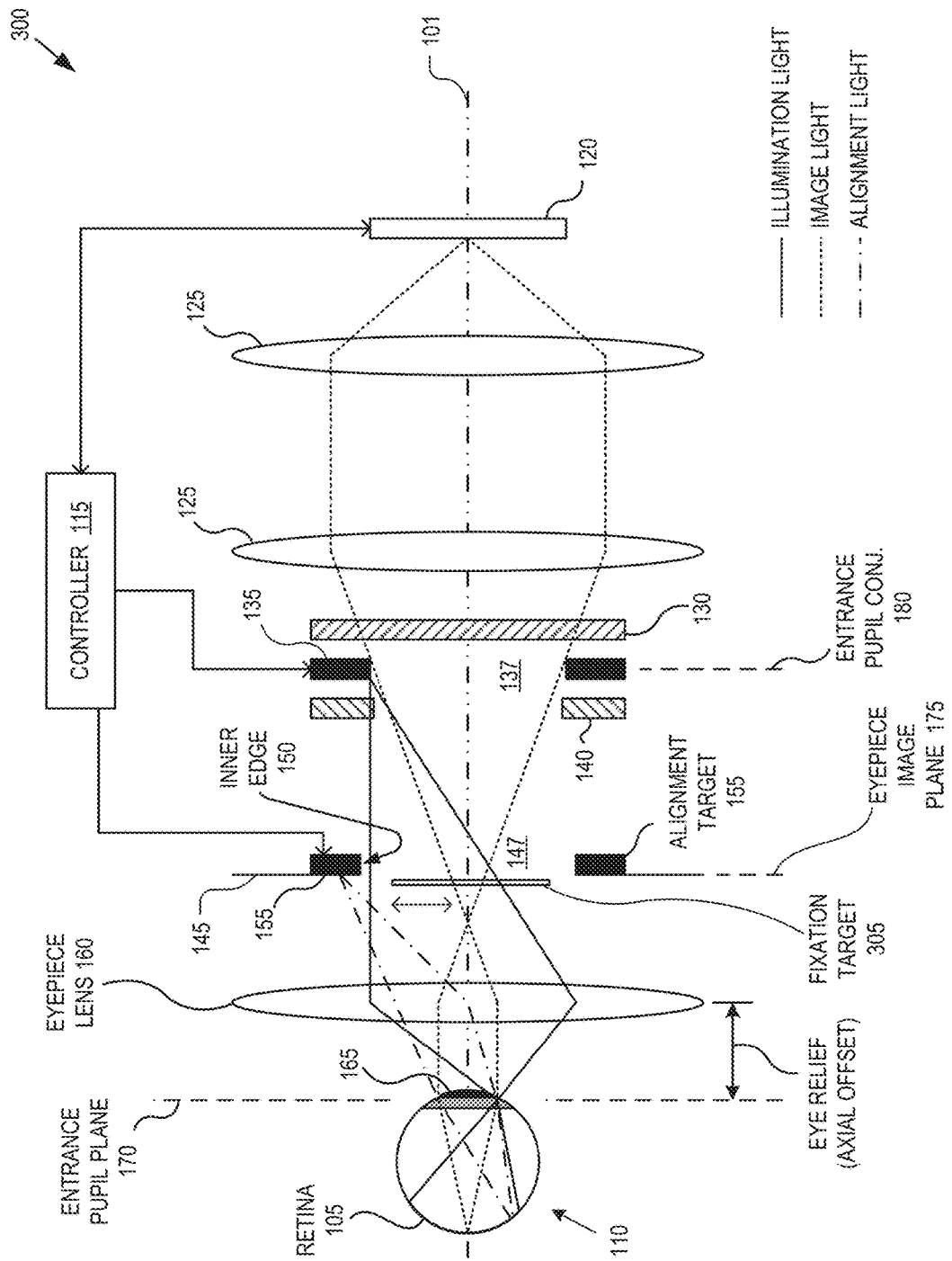
FIG. 3 is an illustration of a fundus camera including a fixation target that aids a user with accommodating to infinity, in accordance with an embodiment of the disclosure.

FIG. 3 illustrates a fundus camera system 300, in accordance with an embodiment of the disclosure. Fundus camera system 300 is similar to fundus camera system 100, except for the addition of a fixation target 305 that operates as a visual aid for eye 110 to accommodate to infinity. In the illustrated embodiment, fixation target 305 is positioned along eyepiece image plane 175 within the user's center of vision, or foveal vision, and provides an image or target for fixation. Fixation target 305 may be a simple dot, pinhole, crosshair, or otherwise. In one embodiment, fixation target 305 is etched or painted on a transparent substrate positioned across aperture 147. In yet another embodiment, fixation target 305 is painted on or formed by a shutter that moves in and out of the user's foveal vision along eyepiece image plane 175. For example, fixation target 305 may be painted on or formed by a shutter that is normally closed, but which rapidly opens by moving out of the imaging path when the user triggers a picture, causing illumination ring 135 to flash illumination light and image sensor 120 to acquire the retinal image. In other embodiments, fixation target 305 is a small, subtle target (e.g., dot or crosshair) that remains stationary. Fixation target 305 may further include its own illumination so that it is viewable by the user. In some embodiments, fixation target 305 may include as a small light source (e.g., LED, fiber tip, etc.) that is placed on a moving target, such as a shutter. In other embodiments, fixation target 305 is a light paint pattern (or etching) on a transparent substrate and is illuminated from the periphery so that the light paint pattern or etching scatters light towards eye 110.

Figure 4:
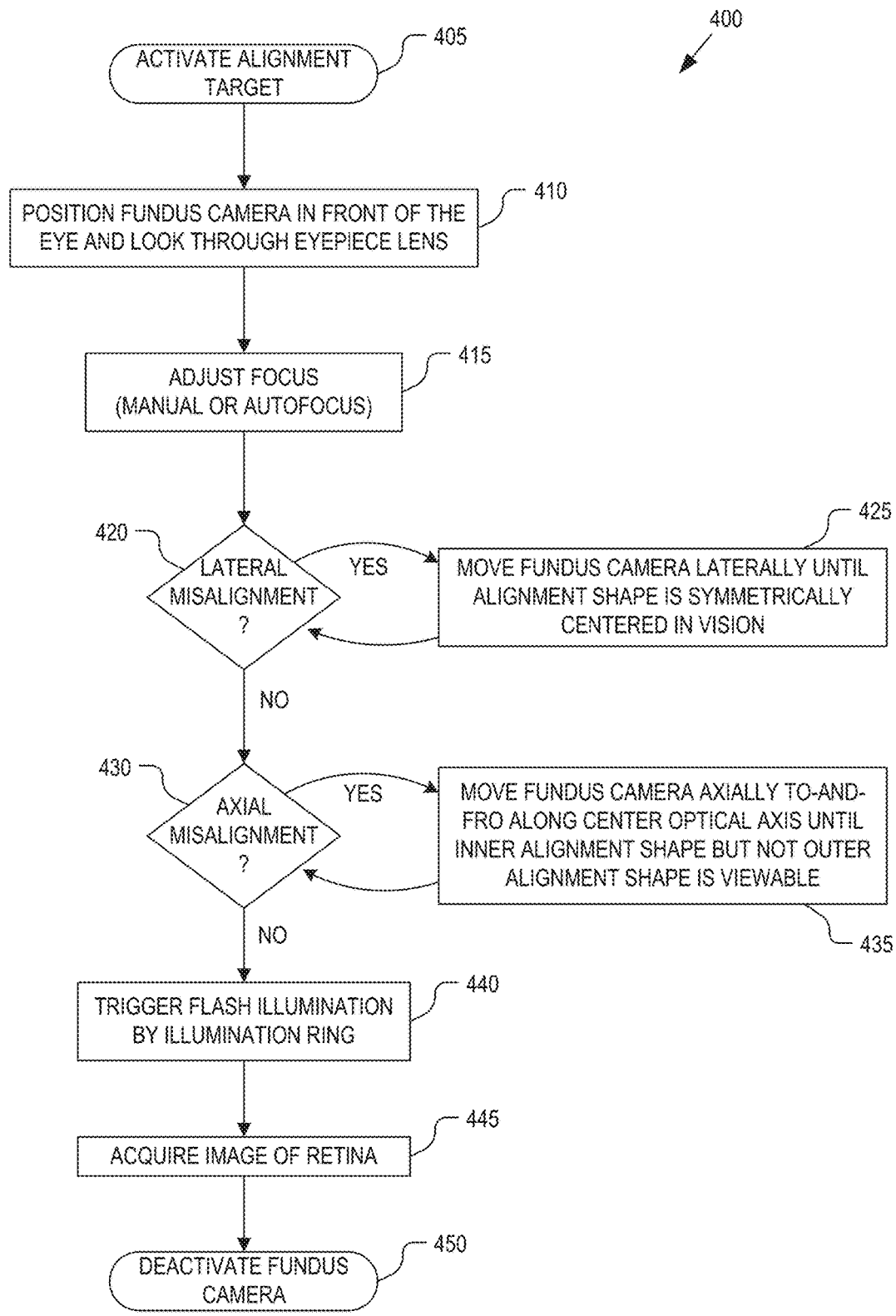
FIG. 4 is a flow chart illustrating a process for self-imaging a retina using a fundus camera, in accordance with an embodiment of the disclosure.

FIG. 4 is a flow chart illustrating a process 400 for self-imaging a retina using fundus camera systems 100 or 300, in accordance with an embodiment of the disclosure. Process 400 is described with reference to FIGS. 5A-5D. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

In a process block 405, controller 115 activates alignment target 155 to output alignment image 205 through eyepiece lens 160 towards eye 110. Alignment image 205 is a peripheral image that is outside the FOV of image sensor 120 and therefore not imaged by image sensor 120. With alignment target 155 (and/or fixation target 305) activated and the user looking through eyepiece lens 160 (process block 410), the user can commence self-alignment and adjust focus. In process block 415, focus can be adjusted in a number of ways to account for different user prescriptions. In a manual focus embodiment, eyepiece lens 160 has a manually adjustable position, which the user can change until alignment image 205 and/or fixation target 305 are in focus. In an autofocus embodiment, an infrared light illuminates retina 105 allowing image sensor 120 to perform an autofocus routine that adjusts the focus of focusing lens(es) 125. In this autofocus embodiment, the user's vision of alignment image 205 or fixation target 305 is not auto-adjusted, though the user can still adjust the relative position of the fundus camera to bring alignment image 205 (and/or fixation target 305) into focus.

In decision block 420 and process block 425, lateral misalignments between pupil 165 and eyepiece lens 160 are corrected until an acceptable lateral alignment (e.g., vertical and horizontal alignment) is achieved. Lateral alignment of pupil 165 is important in order to reduce background noise from iris reflections. If eyepiece lens 160 images the illumination light from ring illuminator 135 offset from pupil 165, this lateral misalignment results in the illumination being focused on the surface of the iris, which causes the diffuse back reflections of the illumination light to enter the imaging path, resulting in high background noise in the retinal image. Thus, it is advantageous to accurately center pupil 165 to eyepiece lens 160 to increase the illumination light entering pupil 165 while reducing deleterious reflections from the iris. One example of achieving this centering is by using an alignment object (e.g., alignment image 205) that is symmetrical about center optical axis 101 to ensure that all sides (or the entire circumference if the alignment target is circular) are seen equally at the periphery of the visual field (e.g., see FIG. 5A or 5D). In this scheme, if the eye is laterally misaligned, the user will see an asymmetric alignment image (e.g., see FIG. 5B). Accordingly, in process block 425, the lateral position between pupil 165 and eyepiece lens 160 is adjusted based upon how the shapes generated by alignment target 155 are centered in the user's vision. In one embodiment, the lateral position is adjusted by the user until the user sees at least one (if not both) of the shapes centered in their vision.

In decision block 430 and process block 435, axial offset (i.e., eye relief) misalignments between pupil 165 and eyepiece lens 160 are corrected until an acceptable axial alignment (e.g., eye relief or axial offset) is achieved. The axial alignment is important to achieve a full illumination/imaging FOV, while avoiding corneal reflections. When eye 110 is too far from the desired eye relief, the illumination and imaging FOVs are decreased as they are obstructed by the iris. When eye 110 is too close, corneal and iris reflections contribute significant background noise in the retinal image. For precise axial alignment, the imaging FOV of eye 110 is used when eye 110 looks at eyepiece image plane 175 through eyepiece lens 160. In a non-pupil forming system, such as the alignment path of fundus camera 100, the overall imaging FOV monotonically increases as the eye moves closer to the eyepiece. Thus, alignment target 155 outputs two shapes (e.g., two concentric rings such as outer shape 210 and inner shape 215) with different sizes and the ring diameters are selected such that only the inner ring can be seen when eye 110 is at the right axial location (e.g., see FIG. 5A). When eye 110 is too far, none of the alignment shapes will be seen in user's FOV (e.g., see FIG. 5C) and when eye 110 is too close, both alignment shapes will be seen in the user's FOV (e.g., see FIG. 5D). Accordingly, in process block 435, the axial offset position between pupil 165 and eyepiece lens 160 is adjusted based upon how many of the shapes of the alignment image are in the user's vision at a given time. For example, the axial offset position is adjusted until the user sees one of the two alignment shapes but not both of the two alignment shapes. If both of the alignment shapes are within the user's FOV (e.g., see FIG. 5D), the axial offset position is increased. If none of the alignment shapes are within the user's FOV (e.g., see FIG. 5C), the axial offset position is decreased by the user.

Figure 5A:
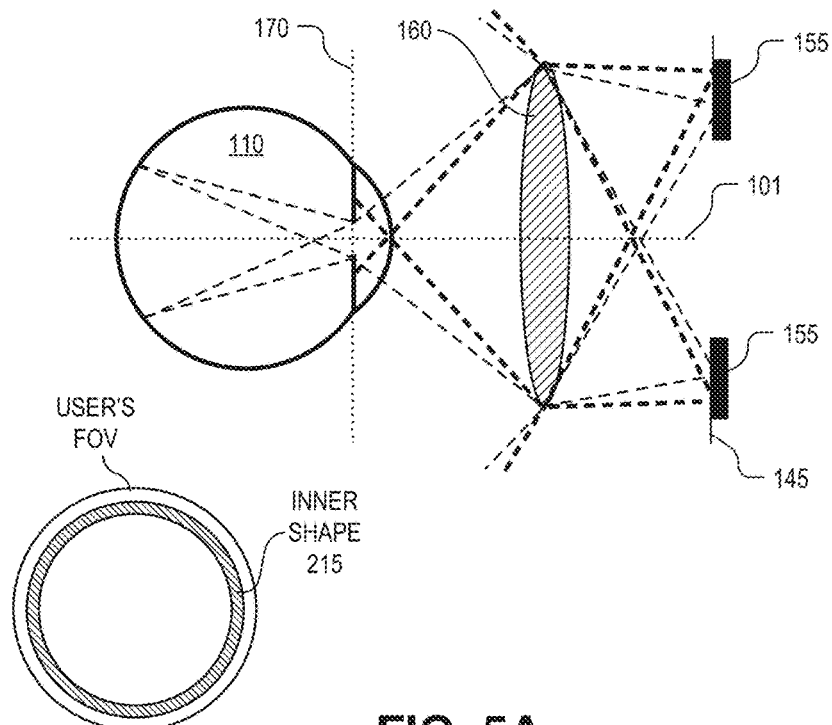
FIGS. 5A-5D illustrate how to use an alignment image output from an alignment target of the fundus camera to self-align a user's eye to the fundus camera, in accordance with an embodiment of the disclosure.
Figure 5B:
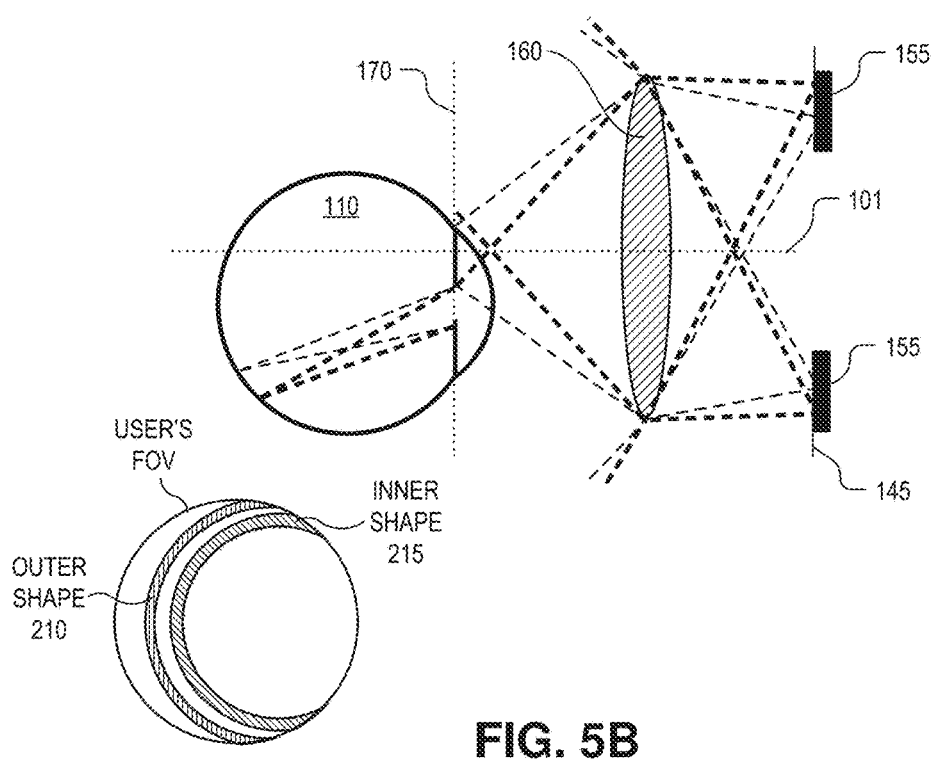
Figure 5C:
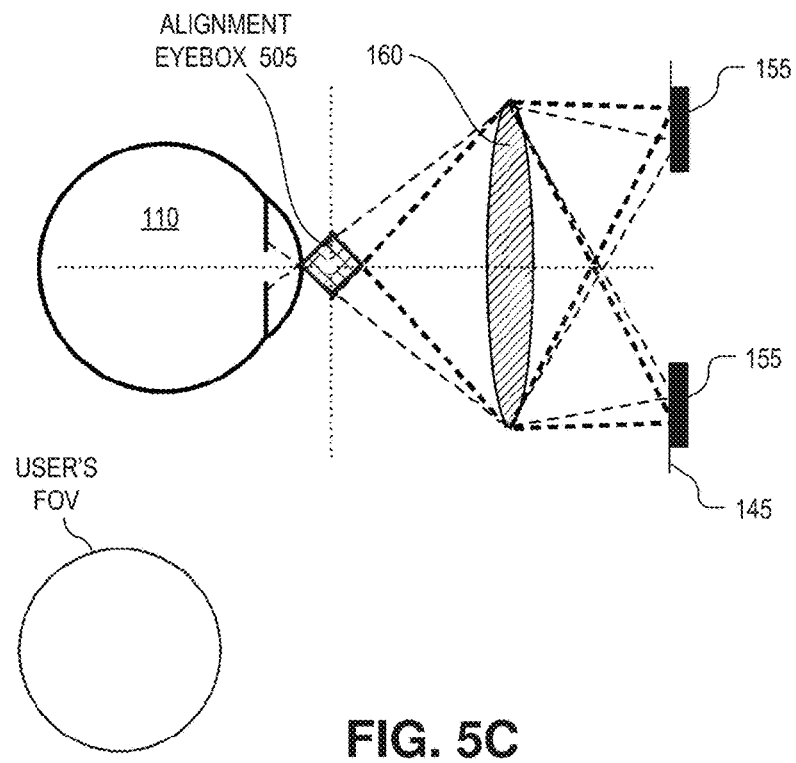
Figure 5D:
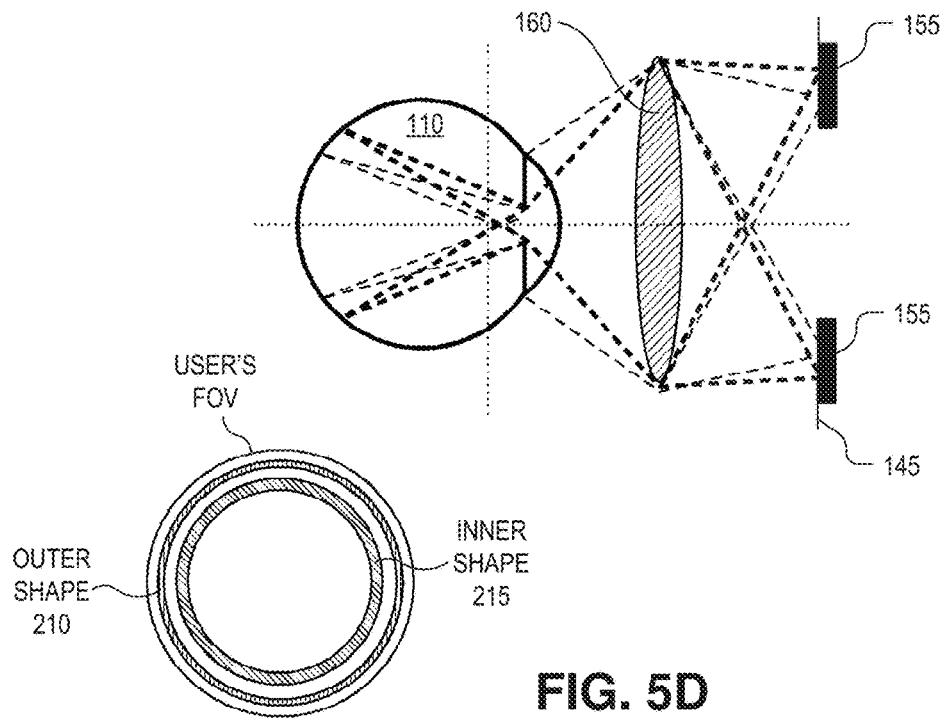

Accordingly, the user will see only a single alignment shape (e.g., inner shape 215) that is symmetrically centered in their FOV when the center of pupil 165 falls within alignment eyebox 505, illustrated in FIG. 5C. The alignment margins can be determined by the size, width, and separation of these alignment shapes output by alignment target 155. Different colors and/or spatial and temporal patterns can be used to distinguish between the inner and outer alignment shapes. Small LEDs, display panels, optical fibers, mask patterns with pinholes, or otherwise can be used to implement alignment target 155 for outputting the alignment image.

Returning to FIG. 4, once the pupil 165 is laterally and axially aligned within alignment eyebox 505, the user can press a shutter button that causes ring illuminator 135 to flash (process block 440) and image sensor 120 to acquire the retinal image (process block 445). In some embodiments, a fixation target is moved out of the imaging path when the user triggers the image acquisition. In a process block 450, the user deactivates the fundus camera and removes their eye from eyepiece lens 160.

Alignment image 205 is designed to match alignment eyebox 505 with a retinal imaging eyebox, such that when the user sees the correct pattern (e.g., only inner shape 215), image sensor 120 also sees the full FOV of retina 105. In order to match these two eyeboxes, the retinal imaging eyebox is designed and measured, and then an alignment target is selected to match the size and the location of alignment eyebox 505 to the retinal imaging eyebox.

Figure 6A:
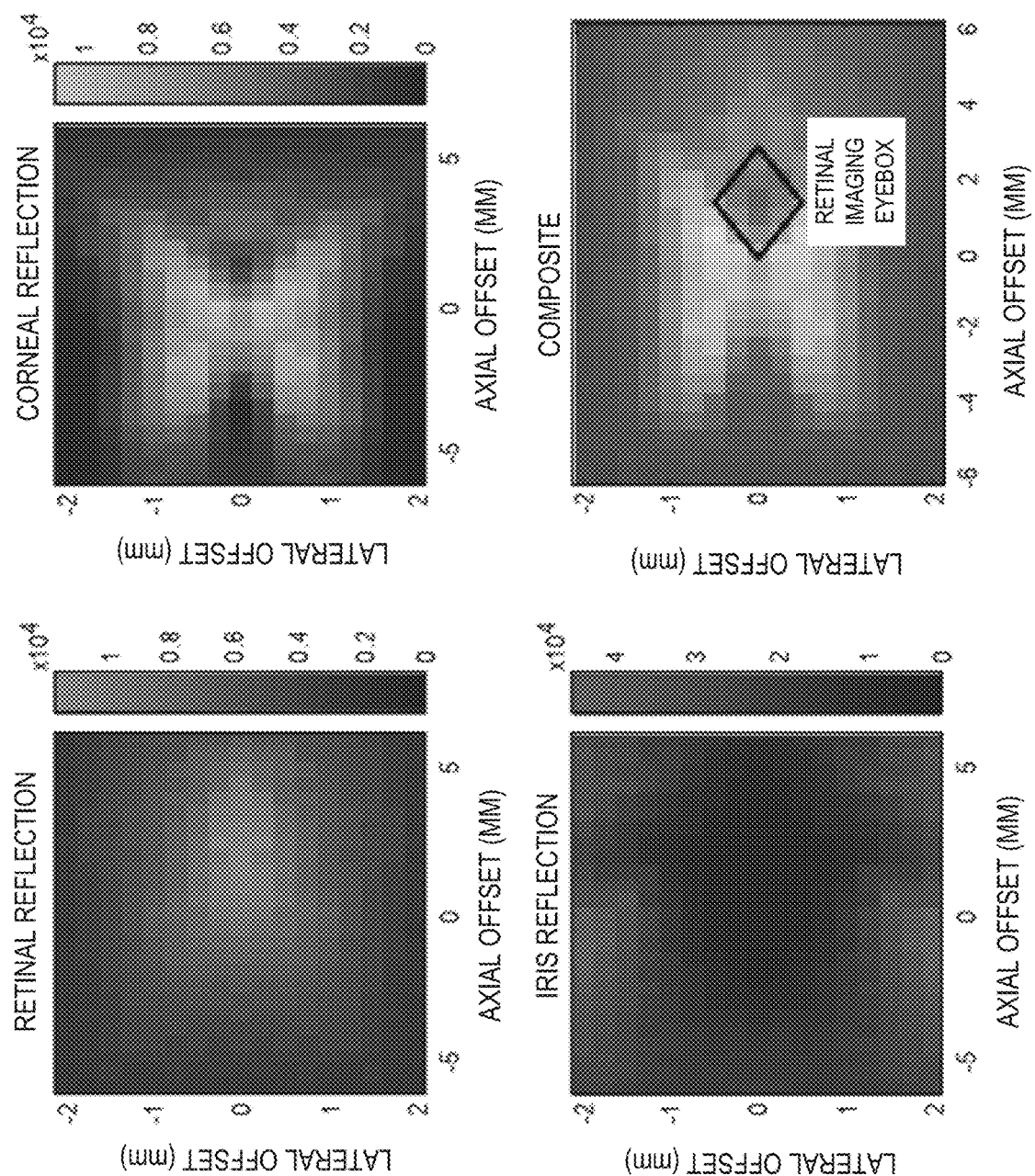
FIG. 6A illustrates the amount of reflection off of eye structures relative to lateral and axial misalignments, in accordance with an embodiment of the disclosure.

The quality of the retinal images is sensitive to the camera-to-eye alignment. Alignment eyebox 505 is defined as a volume of eye alignment margin in which the retinal image quality is acceptable. The size and the location of alignment eyebox 505 is determined by the retinal illumination intensity, retinal reflection collection efficiency, iris reflection, and the corneal reflection at the eye's position relative to image sensor 120. FIG. 6A illustrates the total amount of retinal, iris and corneal reflections collected by image sensor 120 as a function of the eye's lateral and axial position. The retinal imaging eyebox can be found as the highlighted region where the retinal signal collection efficiency is highest and the corneal reflections and the iris reflections are sufficiently rejected.

Figure 6B:
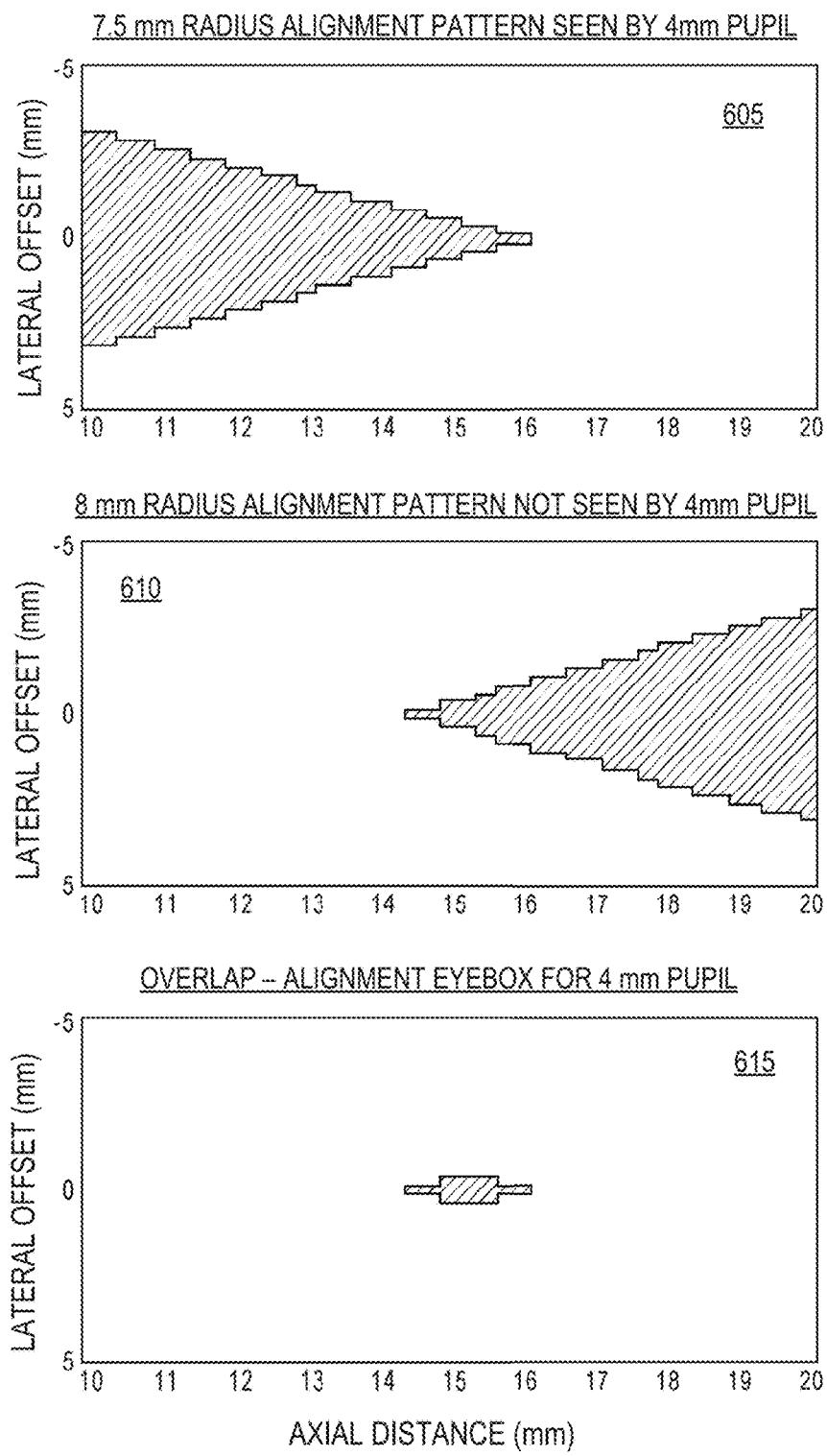
FIG. 6B illustrates how an alignment eyebox is the region of overlap between two eyeboxes, in accordance with an embodiment of the disclosure.

In an alignment scheme using eyepiece imaging plane 175, the imaging FOV increases as eye 105 moves closer to eyepiece lens 160. Alignment eyebox 505 can be determined by an overlapped region of two eyeboxes where: 1) the entire circumference of inner shape 215 is seen (FIG. 6B, graph 605) and 2) none of outer shape 210 is seen (FIG. 6B, graph 610). The overlapped region of these two eyeboxes (FIG. 6B, graph 615) is matched to the retinal imaging eyebox by changing the sizes of the two alignment shapes (e.g., outer shape 210 and inner shape 215).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A fundus camera, comprising:
an illumination source adapted to shine illumination light on a retina of an eye;
an image sensor disposed for capturing image light as a reflection of the illumination light off of the retina;
an eyepiece lens disposed to pass the image light from the retina to the image sensor; and
an alignment target positioned on an image plane of the eyepiece lens to output an alignment image through the eyepiece lens to the eye, wherein the alignment target is disposed around a first field stop having a first aperture through which the image light is passed to the image sensor such that the alignment image is outside of a field of view of the image sensor.

2. The fundus camera of claim 1, wherein the illumination source comprises an illumination ring defining a second aperture, wherein a backside of the illumination ring forms a second field stop that limits the field of view of the image sensor placing the alignment image outside the field of view of the image sensor.

3. The fundus camera of claim 2, wherein the illumination ring is positioned to direct the illumination light through the first aperture to illuminate the retina with the illumination light.

4. The fundus camera of claim 2, wherein the illumination ring and an emissive aperture of the alignment target that outputs the alignment image are physically positioned to be coaxially aligned around a center optical axis.

5. The fundus camera of claim 1, wherein the alignment image comprises two concentric and symmetric shapes and wherein the two concentric and symmetric shapes provide visual cues that facilitate self-alignment of the fundus camera to the eye.

6. The fundus camera of claim 5, wherein the two concentric and symmetric shapes include an inner shape and an outer shape, and wherein the inner and outer shapes are configured to provide a first visual cue for adjusting a lateral position of the fundus camera relative to the eye.

7. The fundus camera of claim 5, wherein the inner and outer shapes are configured to provide a second visual cue for adjusting an axial offset position between the eye and the eyepiece lens.

8. A fundus camera, comprising:
an image sensor for capturing image light of a retina within an eye;
an eyepiece lens disposed to pass the image light of the retina to the image sensor;
an illumination ring disposed to direct illumination light onto the retina through the eyepiece lens, the illumination ring disposed around a first aperture through which the image light of the retina passes from the eyepiece lens to the image sensor; and
an alignment target positioned to output an alignment image through the eyepiece lens to the eye, the alignment target disposed around a second aperture through which the image light of the retina is passed to the image sensor and the illumination light is passed to the eyepiece lens.

9. The fundus camera of claim 8, wherein the alignment target and the alignment image are outside a field of view of the image sensor.

10. The fundus camera of claim 9, further comprising:
a field stop,
wherein the field stop and the alignment target are positioned between the eyepiece lens and the illumination ring on a common plane, and
wherein the alignment image of the alignment target is emitted peripherally of an inner edge of the field stop and directed towards the eyepiece lens.

11. The fundus camera of claim 8, wherein the illumination ring and an emissive aperture of the alignment target are physically positioned to be coaxially aligned around a center optical axis.

12. The fundus camera of claim 11, wherein the eyepiece lens and the image sensor are also physically positioned to be coaxially aligned around the center optical axis.

13. The fundus camera of claim 8, wherein the alignment target is positioned along an image plane of the eyepiece lens which is a conjugate plane to the retina when the eye is fixated at infinity and aligned to the fundus camera and the illumination ring is positioned at or near a conjugate plane to an entrance pupil of the eye when the fundus camera is aligned to a retinal imaging eyebox.

14. The fundus camera of claim 8, wherein the alignment target outputs the alignment image as a visual cue that facilitates self-alignment of the fundus camera to the eye.

15. The fundus camera of claim 8, wherein the alignment image comprises two concentric and symmetric shapes.

16. The fundus camera of claim 15, wherein the two concentric and symmetric shapes comprise an outer circle having a first color and an inner circle having a second color different from the first color.

17. The fundus camera of claim 8, further comprising:
a polarizing ring disposed between the illumination ring and the alignment target and orientated to linearly polarize the illumination light along a first polarization axis; and
a polarizing plate disposed between the illumination ring and the image sensor and orientated to linearly polarize the image light of the retina along a second polarization axis orthogonal to the first polarization axis.

18. The fundus camera of claim 8, further comprising:
at least one focusing lens disposed between the illumination ring and the image sensor to focus the image light of the retina onto the image sensor.

19. The fundus camera of claim 8, comprising:
a fixation target disposed along an image plane of the eyepiece lens to provide a visual aid for the eye to accommodate to infinity.

20. The fundus camera of claim 8, comprising:
a fixation shutter disposed along the image plane of the eyepiece lens, wherein the fixation image is disposed on or defined by the fixation shutter and wherein the fixation image is moveable into and out of the eye's foveal vision along the image plane of the eyepiece lens.

21. A method of operation of a fundus camera, the method comprising:
directing illumination light from an illumination ring through an eyepiece lens and a first aperture towards a retina of an eye, wherein an alignment target is disposed around the first aperture and the illumination ring is disposed around a second aperture;
outputting an alignment image from the alignment target through the eyepiece lens towards the eye as a visual aid for aligning the eyepiece to the eye;

passing image light, that is a reflection of the illumination light off of the retina, through the eyepiece lens, the first aperture, and the second aperture to an image sensor; and capturing the image light of the retina with the image sensor to generate a retinal image.

22. The method of claim 21, wherein the alignment target and the alignment image are outside a field of view of the image sensor.

23. The method of claim 21, wherein the alignment image comprises two concentric and symmetric shapes.

24. The method of claim 21, wherein the illumination ring and an emissive aperture of the alignment target are physically positioned to be coaxially aligned around a center optical axis.

25. The method of claim 21, further comprising:
moving a fixation target out of a field of view of the image sensor when capturing the image light, wherein the fixation target provides a visual aid for accommodating to infinity.

* * * * *